United States Patent

Baccanti et al.

Patent Number: 5,571,480
Date of Patent: Nov. 5, 1996

[54] DEVICE FOR FEEDING SAMPLES TO ELEMENTAL ANALYSIS APPARATUSES

[75] Inventors: Marco Baccanti, Rodano; Paolo Magni, Besana in Brianza; Camillo Rena, Brescia; Elio Bassi, Soresina, all of Italy

[73] Assignee: Fisons Instruments S.p.A., Rodano, Italy

[21] Appl. No.: 113,431

[22] Filed: Aug. 27, 1993

[30] Foreign Application Priority Data

Aug. 31, 1992 [IT] Italy .................................. MI92A2035

[51] Int. Cl.⁶ ...................................... G01N 35/10
[52] U.S. Cl. ............................ 422/103; 422/63; 422/100; 436/180
[58] Field of Search ..................... 422/100, 103, 422/104, 199, 63, 64, 81, 94, 93, 83; 436/180, 179, 47, 48

[56] References Cited

U.S. PATENT DOCUMENTS

| | | |
|---|---|---|
| 4,055,259 | 10/1977 | Sibrava . |
| 4,244,919 | 1/1981 | Chen ........................................ 422/100 |
| 4,351,801 | 9/1982 | Bartke . |
| 4,462,963 | 7/1984 | O'Brien et al. ........................... 422/78 |
| 4,746,491 | 5/1988 | Öhlin ...................................... 422/103 |
| 4,920,056 | 4/1990 | Dasgupta ................................. 436/50 |
| 5,213,763 | 5/1993 | Richecoeur et al. .................... 422/100 |

FOREIGN PATENT DOCUMENTS

| | | |
|---|---|---|
| 0280335 | 7/1990 | European Pat. Off. . |
| 0585802A3 | 9/1994 | European Pat. Off. . |
| 1221800 | 6/1960 | France . |
| 1802261 | 11/1970 | Germany . |
| 9209327 U | 11/1992 | Germany . |

Primary Examiner—Long V. Le
Attorney, Agent, or Firm—Millen, White, Zelano, & Branigan, P.C.

[57] ABSTRACT

A device for automatically feeding samples to an elemental analysis combustion apparatus. The device has a housing for the sample and is rotatable from an external sample receiving position to a sample feeding position. The housing is insulated from the atmosphere and is connected to the combustion apparatus. The moving body is a truncated cone which is rotatable about its axis within a seat.

8 Claims, 2 Drawing Sheets

DEVICE FOR FEEDING SAMPLES TO ELEMENTAL ANALYSIS APPARATUSES

BACKGROUND OF THE INVENTION

1. Field of the invention

The present invention relates to a device for sample feeding to combustion elemental analysis apparatuses. The device is of the type comprising a housing for the sample to be analyzed, said housing being provided in a movable support. The latter moves from a position where sample is received to a position of sample injection into the analytical instrument. In this position perfect sealing of the apparatus from external environment must also be ensured.

In the device, in correspondence with the movable support, the circulation of an inert gas is also foreseen for washing the sample housing.

2. Description of the Prior Art

Similar devices, already known in the art, receive a sample, generally contained in an envelope made of metal (e.g. tin), that must be submitted to qualitative and quantitative analysis of its components.

Obviously, the sample introduction into the analytical detection system must ensure that no other substances capable of altering the analysis are fed therewith, such as for example air present in the environment outside the apparatus.

For this purpose, combustion elemental analysis is performed in an atmosphere of inert gas, generally helium, that is used in the analytical apparatus both as sample washing gas and as carrier gas. This therefore involves a particularly accurate configuration in order to ensure perfect sealing, mainly in correspondence with the reciprocally moving parts, in order to avoid infiltrations of foreign elements that can affect analytical precision. Italian Patent IT 1122396, filed by Carlo Erba Strumentazione S.p.A., provides a sampler of the aforedescribed type, wherein a slide, sealingly movable within a seat, moves from a position where the sample coming from the external environment is received to a position where the sample is fed to the analytical apparatus, also ensuring in the latter position the insulation of the analytical environment from the external atmosphere.

The reciprocating movement of the slide is obtained by means of a double-acting cyclinder-piston pneumatic system. This solution is effective from the sealing point of view, but involves a considerable complication of the mechanisms driving the slide to achieve the necessary precision. Furthermore, possible increases in the number and size of the samples to be treated require to enlarge or replace the operating system thus jeopardizing the precision of movements and resulting in loss of reliability of the device.

A further drawback of the known devices is the fact that, with the slide use, particles of the analyzed samples fall on the slide and their accumulation leads to an increase in the sliding friction and therefore to an accelerated wear of the slide up to loss of sealing. Furthermore, maintenance operations become long and expensive due to the aforementioned complexity of the operating mechanisms of the device.

Said drawbacks are particularly important in the case of automatic feeders.

SUMMARY OF THE INVENTION

It is the aim of the present invention to provide an improved device that reduces or eliminates said drawbacks of known samplers.

This aim is achieved by providing a device for sample feeding to an apparatus for combustion elemental analysis (i.e. ultimate analysis), of the type comprising supporting means provided with a housing for the sample to be analyzed, said supporting means being movable from a position where said housing receives the sample to a position where said housing releases the sample into the analytical apparatus, characterized in that said support substantially consists of a body rotatable about its axis within a seat having conjugated shape and dimensions.

A better sealing of the device is thus obtained while simplifying the operating mechanism of the movable supporting means.

A further advantage is given by the mechanical simplicity of the device according to the invention, considerably facilitating its maintenance, that can be performed directly by the end user.

This becomes particularly advantageous in the case where the sampler is of the automatic type. The following description will be referred to such a type of sampler, with however no intention of restricting the invention thereto.

BRIEF DESCRIPTION OF THE DRAWINGS

Further features and advantages will become clearer from the following description given with illustrative and non limiting purposes with reference to the accompanying drawings, where.

DETAILED DESCRIPTION

Figure 1:
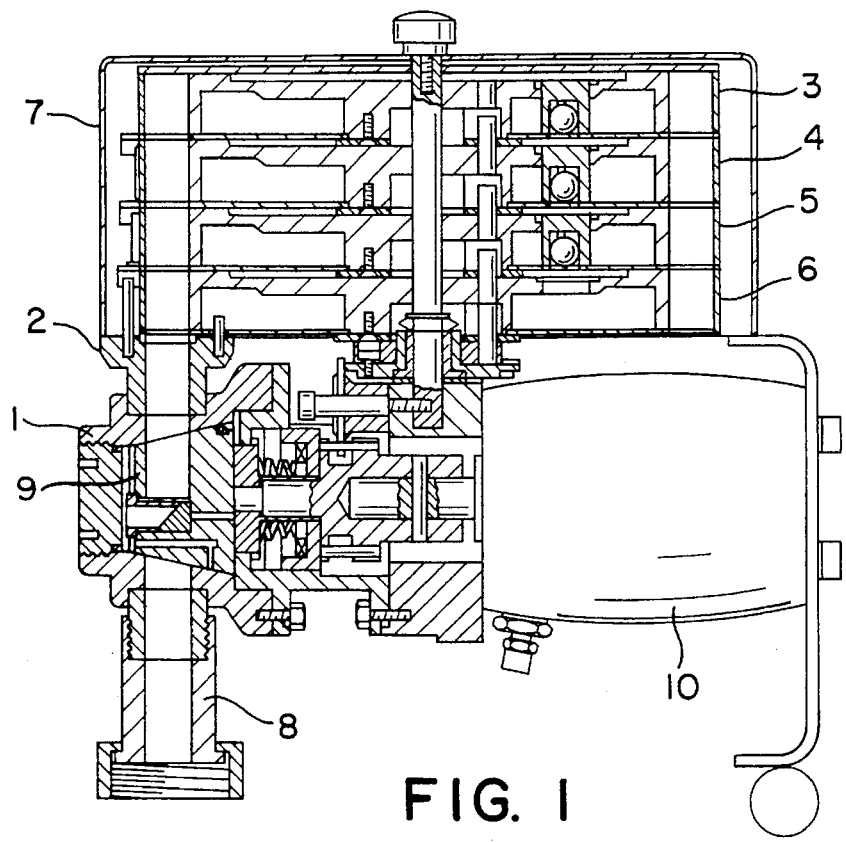
FIG. 1 is a cross sectional view of the device according to a preferred embodiment of the invention.

FIG. 1 shows a device according to the invention that comprises a chamber 1 connected upstream with a fitting 2 for the introduction of the sample coming from a delivering unit provided with rotary disks 3, 4, 5, 6, provided inside a cover 7 made of transparent material.

The chamber 1 of the device is connected downstream with a fitting 6 to feed the sample to the reactor of the analytical apparatus (not shown).

Inside chamber 1 of the device there is provided a seat within which moving body 9 is engaged with possibility of movement of rotation about its own axis. Substantially, while in the state of the art the movement of the moving body from the position where the sample is received to the position where it is fed to the combustion reactor was of translational type, according to the invention said movement if of rotational type.

Figure 2:
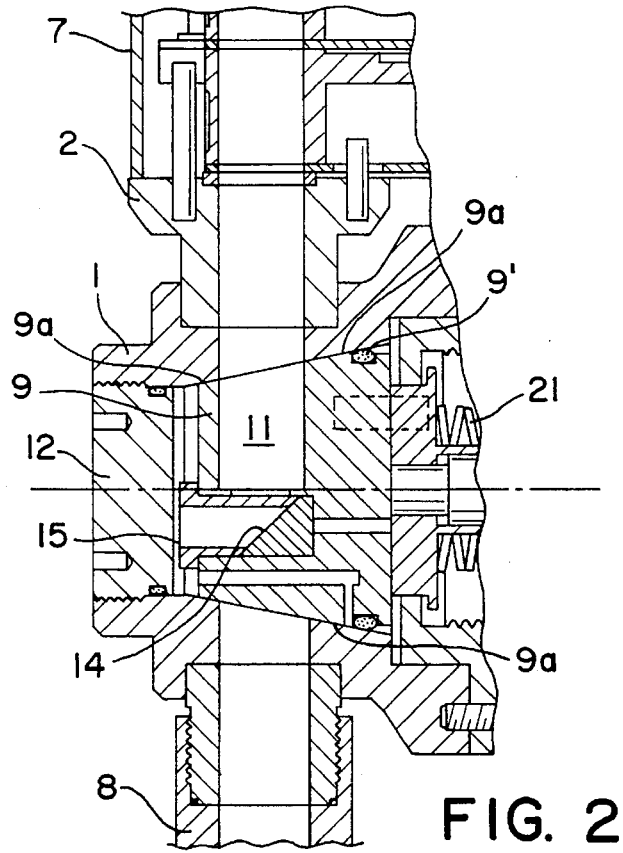
FIG. 2 is an enlarged cross sectional view of a detail of FIG. 1.

According to a preferred embodiment of the invention as shown in FIG. 2, the moving body 9 has a substantially truncated cone shape 9a, since the latter, together with the conjugated shape and dimensions of the seat, ensures an optimal sealing without however preventing the relative movement of the body 9 with respect to its seat.

The movement of rotation of the body 9 is preferably obtained by means of a pneumatic actuator 10. The rotational axis of body 9 corresponds to the axis of the actuator 10 and, through means of motion transmission that also transmits movement of synchronized rotation to the sample delivering unit placed on top of the device.

FIG. 2 more clearly illustrates the structure of the body 9 in the position, in contact with outside environment, where the sample is received into housing 11 and the housing is directed upward. The housing 18 in a transverse position with respect to the axis of rotation of body 9, and is also aligned upstream with the inlet of the injection duct 2 and downstream with the coaxial opening of duct 8 connected to the combustion reactor of the analytical apparatus (not shown).

The moving body 9 is provided in a known way with at least one sealing gasket 9' and is urged into the sealing position by Belleville washers 21 or similar elastic means.

This enables to transfer the sample with a simple movement of rotation according to a preset angle, that in the case of the preferred embodiment is of 180 degrees, (the housing 9b then directed downwards) while maintaining at the same time a perfect insulation of the analytical environment from the atmosphere and to deliver the sample to duct 8 which is connected to the reactor.

The introduction of the sample and its subsequent combustion can be visually controlled through a portion 12 made of transparent material removably fixed on the front wall of the device in correspondence with the body 9. The latter comprises a channel 13 (FIGS. 3, 4), parallel to its axis of rotation, inside which a sloping reflecting surface 14 and a lens 15 make visible to the outside the images coming from inside the combustion reactor.

Figure 3:
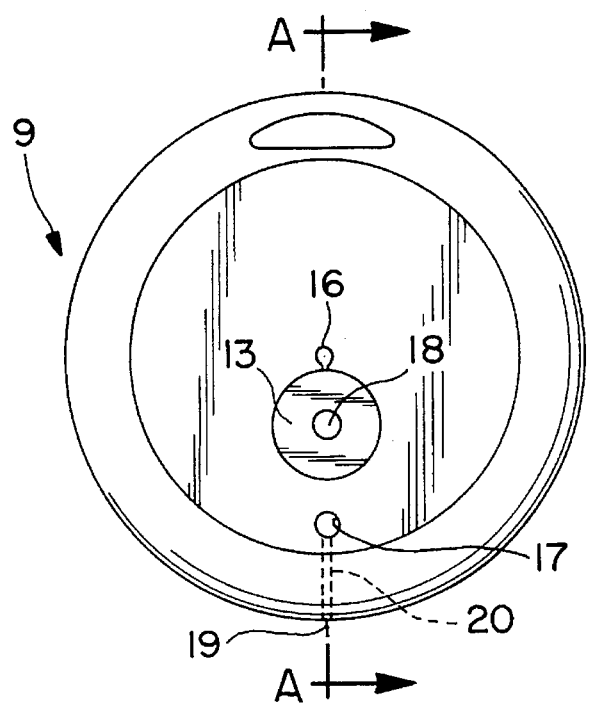
FIG. 3 is a front view of the rotatable body according to the invention.

FIG. 3 is a front view of septum 9 where the presence of the openings of a series of ducts 16, 17, 18 for the circulation of inert gas for sample washing is highlighted.

Helium is generally used as washing inert gas and preferably the washing gas and the carrier gas are the same.

The use of an inert gas for washing the sample before the analysis allows to perform combustion in an environment totally deprived of air or of other elements that can affect the analytical result. The inert gas is moreover fed at a pressure exceeding the atmospheric pressure or in any case such as to ensure the sealing of the device with respect to the external atmosphere.

Figure 4:
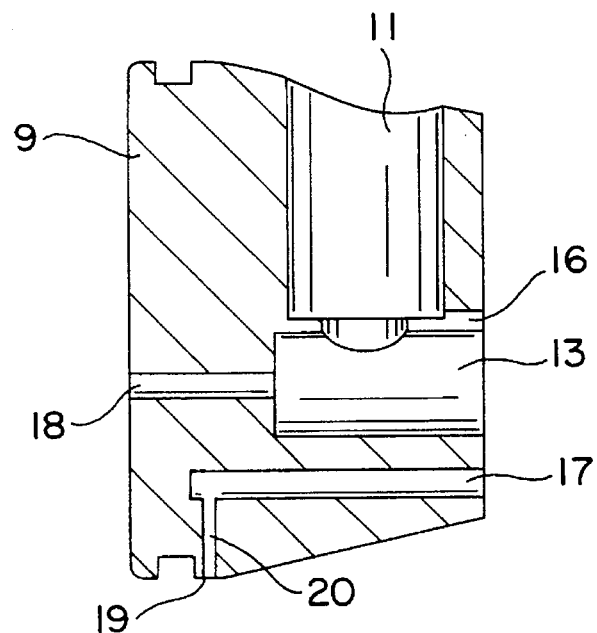
FIG. 4 is a sectional view along line A—A of FIG. 3 of the rotatable body.

As better shown in FIG. 4, the washing gas is fed through a port 19 of a first duct 20 communicating with the duct 17 inside the body 9. The duct 17 allows the washing gas to flow into the front interstice of the seat where the body 9 is positioned. The duct 16 allows the washing gas to flow into the housing 11 of the sample while the duct 19 and the O-ring housing are in communication.

In this way the back side of the body 9 is pneumatically connected to the duct for feeding washing gas, so as to obtain perfect sealing under pressure of the analytical environment with respect to the atmosphere.

We claim:

1. A sampling device for feeding samples to a combustion elemental analysis apparatus comprising a chamber having:
   (a) first means for receiving a sample from a delivering unit;
   (b) second means for releasing the sample into the apparatus for analysis;
   (c) said chamber further including a seat having a conjugated shape, sample supporting means having a housing means; and biasing means for urging said sample supporting means against said seat, wherein said sample supporting means is substantially a truncated cone and is rotatable about its own axis between a first position wherein said housing means is connected to said first means for receiving the sample therefrom and a second position wherein said housing means is Connected to said second means and is insulated from ambient atmosphere for releasing the sample into the apparatus for analysis, and wherein said sample supporting means and said seat are complementary for substantially sealing said sample supporting means during rotation between said first position and said second position.

2. The device of claim 1 wherein said sample supporting means is rotatable about a rotational axis and said housing means is substantially transverse the rotational axis of said sample supporting means.

3. The device of claim 2, wherein said first and second positions are coaxially aligned.

4. The device of claim 1, wherein said sample supporting means further comprises at least one duct means for connecting to said seat and said housing for purging ambient air.

5. The device of claim 1, wherein said sample supporting means is rotatable about a rotational axis and further comprises a channel parallel to the rotational axis of said sample supporting means; and visual inspection means within said channel.

6. The device of claim 5, further comprising transparent material aligned with said visual inspection means and spaced therefrom, wherein said inspection means comprises a sloping reflecting surface located between said channel and said ample housing, and a lens positioned within said channel.

7. A device according to claim 1, wherein said sample delivery unit has at least one rotary disk and actuating means for stepwise controlling rotation of said disk and said sample supporting means.

8. A device according to claim 7, wherein said actuating means is a pneumatic actuator.

* * * * *